United States Patent
Zobele

(10) Patent No.: US 7,082,259 B2
(45) Date of Patent: Jul. 25, 2006

(54) ELECTRIC VAPORISER OF FRAGRANCES OR INSECTICIDES, WITH EVAPORATION INTENSITY ADJUSTMENT FUNCTION

(75) Inventor: Franco Zobele, Trento (IT)

(73) Assignee: Zobele Holding S.p.A., Trento (IT)

( * ) Notice: Subject to any disclaimer, the term of this patent is extended or adjusted under 35 U.S.C. 154(b) by 0 days.

(21) Appl. No.: 11/071,214

(22) Filed: Mar. 4, 2005

(65) Prior Publication Data

US 2005/0196159 A1 Sep. 8, 2005

(30) Foreign Application Priority Data

Mar. 4, 2004 (IT) .......................... MI2004A0416

(51) Int. Cl.
*F24K 6/00* (2006.01)

(52) U.S. Cl. ....................................... 392/390; 392/392
(58) Field of Classification Search ................ 392/386, 392/390, 391, 392, 393, 394, 395; 239/44, 239/49, 50; 122/366
See application file for complete search history.

(56) References Cited

U.S. PATENT DOCUMENTS 6,466,739 B1 * 10/2002 Ambrosi et al. ............ 392/395
6,580,875 B1 * 6/2003 Rymer ........................ 392/395

* cited by examiner

*Primary Examiner*—Sang Paik
(74) *Attorney, Agent, or Firm*—Young & Thompson

(57) ABSTRACT

Electric vaporiser for a fragranced or insecticidal active substance with adjustment of the evaporation intensity, includes a support technical body, onto which a porous element impregnated with the active substance and an electric heating device located in the proximity of the porous element are fixed, in order to determine the evaporation of the active substance in an evaporation area. The electric heating device is housed in a drawer which is movable in a direction substantially perpendicular to the porous element, between a position of maximum evaporation intensity, near or adjacent to the porous element, and a position of minimum evaporation intensity, far from the porous element. The control mechanism which causes the shifting of the electrical device includes a variable-radius cam obtained in an adjustment disc, with which a pin integral with the drawer and protruding therefrom engages; the mechanism is located entirely outside the evaporation area.

14 Claims, 4 Drawing Sheets

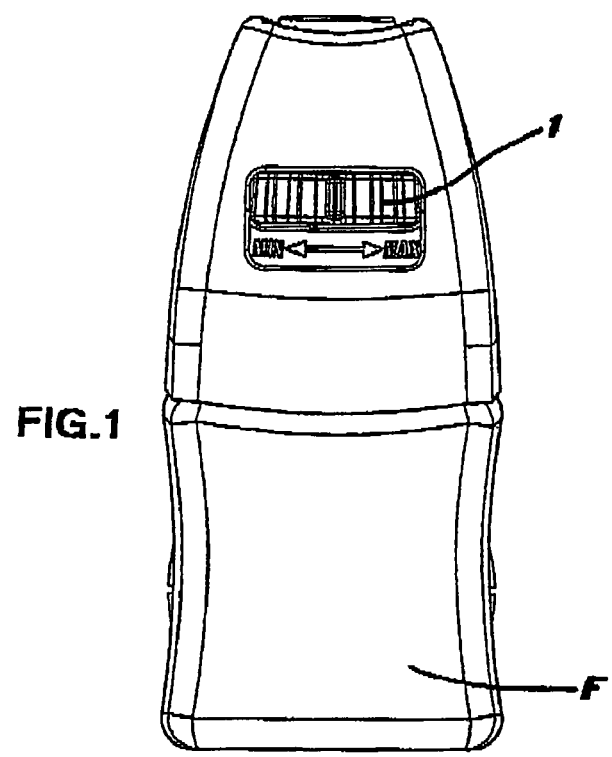
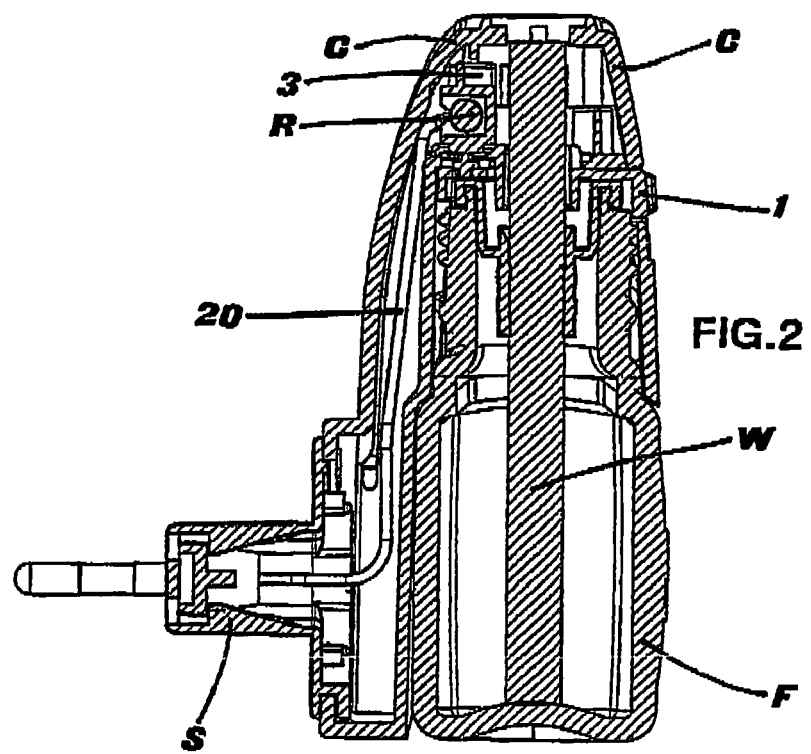

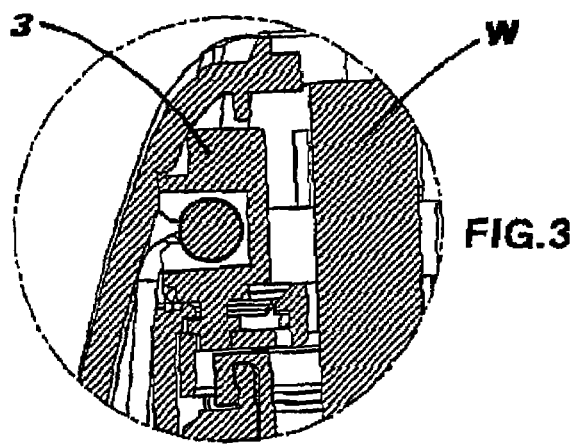
FIG.3 min
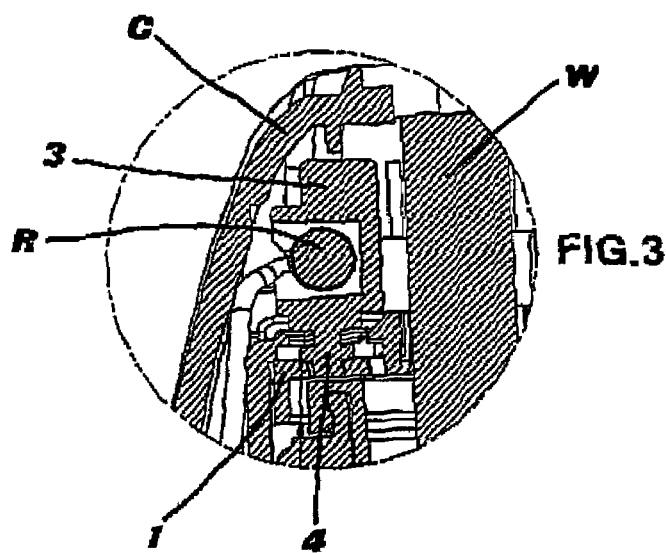
FIG.3
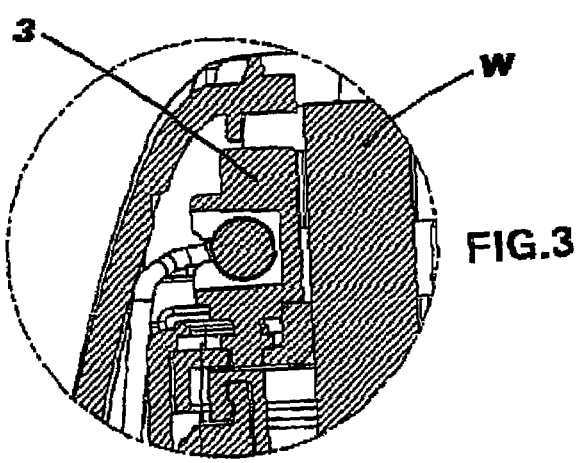
FIG.3 max

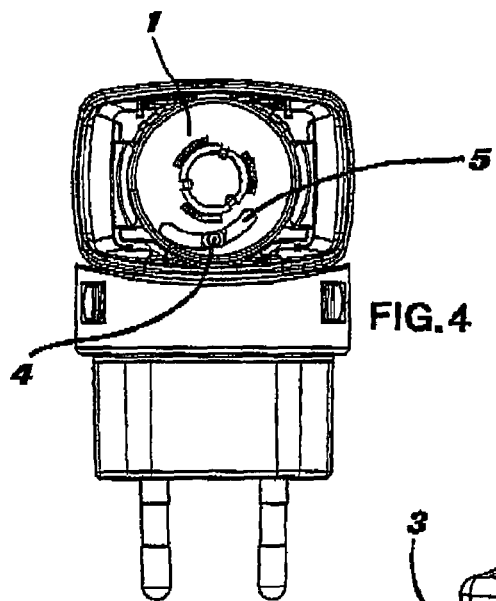
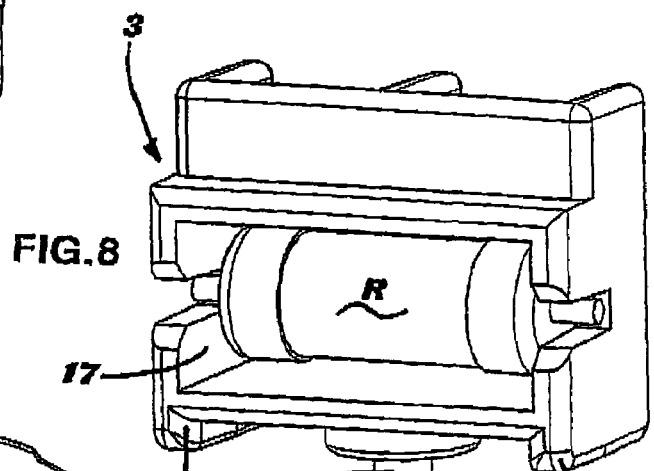
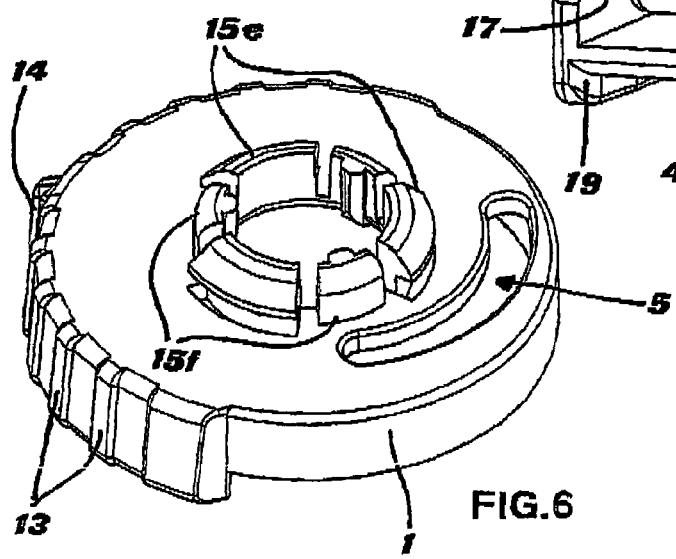

ELECTRIC VAPORISER OF FRAGRANCES OR INSECTICIDES, WITH EVAPORATION INTENSITY ADJUSTMENT FUNCTION

The present invention relates to an electric vaporiser of fragrances or insecticides, wherein it is possible to adjust the evaporation intensity of the active substance between a minimum value and a maximum value, by varying the flow of the heat transmitted to the porous support impregnated with said active substance.

More specifically, the present invention relates to an electric vaporiser of fragrances or insecticides in liquid formulations, wherein the active substance is contained in an airtight bottle. A bottle houses a porous wick, which partly protrudes from the bottle neck passing in the proximity of an evaporation area of the vaporiser. The vaporiser in fact comprises an electric heating device—normally in the shape of an electric resistance or of a PTC—and by the expression "evaporation area" the area is in fact intended wherein the heat flow generated by said electric heating device spreads over the wick determining the evaporation of the active substance contained therein and thereby the desired operation of the vaporiser, while fresh active substance is continuously withdrawn from the bottle into the wick due to the capillary effect.

In the field of domestic electric vaporisers used with liquid formulations, vaporisers are already known which allow to adjust the evaporation intensity of the active substance by modifying the mutual position of the heating device and of the wick.

These known devices can be divided into different categories, which will be briefly discussed in the following, also highlighting the main drawbacks that can be found therein.

In a first vaporiser category, the heating device is fixed and the bottle, with its wick, is shifted along the axis thereof by a mechanical device, for example of the screw/nut type or more simply of the friction type, in order to increase or decrease the evaporation area, i.e. the area where wick and heating device overlap; a device of this type is described for example in EP-A-0942648. A solution of this type has the advantage of a simplified construction of the heating device and of the corresponding electrical connections, indeed due to the fact that such device is fixed; however, vaporisers using a screw/nut mechanism for axially shifting the bottle, have the drawback—due to the high number of components they consist of and to the consequently high cost of the fitting operations which need to be carried out, at least partly, manually—of a high manufacturing cost; for the friction-type ones, which are instead of a simpler and cheaper construction, the main drawback lies in their awkwardness during use and in the poor stability of the desired adjustment position in case of involuntary manipulations.

In a second category of vaporisers, the heating device is integral with the plug and rotating therewith, as described for example in EP-A-0943344. The plug body is further manufactured in such a way, with a screw/nut or eccentric device, as to allow axial or lateral shifting of the body itself, and consequently of the heating device, with respect to the wick, in the different possible positions taken up by the plug. In these devices also it is hence achieved a simple and problem-free construction of the heating device and of its respective electrical connections, which are of course subject to no mutual shifting during plug rotation, but there remains the problem of still too high a manufacturing cost—although lower than the one of the devices of the previous category—which is due to the fact that not a standard rotary plug is used, but rather a purpose-build plug. Moreover, adjustment of evaporation intensity is possible only between two positions, of minimum flow and of maximum flow, respectively, therefore without the possibility of continuously and precisely adjusting evaporation intensity between a minimum value and a maximum value.

In a third and last vaporiser category, it is instead the heating device which is movable, and it is driven closer to or further apart from the wick of the bottle containing the liquid active solution, thanks to a mechanic device of the screw/nut type, so as to increase or decrease the heat flow which spreads over the wick itself. Such a device is disclosed for example in ES-U-1015255. The main drawbacks of this type of vaporisers lie, on one hand and as already seen above with reference to vaporisers of the first category, on the high manufacturing cost of the mechanical screw/nut device and, on the other hand, on the safety and duration of the electrical connections between the plug and the heating device, which connections are necessarily subject to continuous movement during adjustment operations on the vaporiser. Finally, adjustment of evaporation intensity is rather approximate, both as far as consistency of the minimum and maximum values is concerned, and especially as far as repeatability and linear variation of the intermediate values is concerned. As a matter of fact, the heating device shiftings often determine an irregular alteration of heat flow distribution, due to the fact that the different moving parts of the device create varying obstacles to said flow.

The object of the present invention is precisely to provide an electric vaporiser of insecticides or fragrances belonging to the third category described above, wherein, however, optimal and continuous adjustment of the flow of the evaporated active substance can be obtained, which flow is comprised between a minimum flow and a maximum flow, with no need to employ complex mechanical systems of the screw/nut type and further preventing the inevitable shiftings of the electrical connections of the heating device during adjustment operations of the evaporation flow from compromising the safety and duration of said connections.

Another object of the present invention is further to provide a vaporiser of the aforementioned type wherein the evaporation area contains no moving components located between the wick and the heating device, which components may varyingly alter or shield the heat flow in the different mutual positions between the wick and the heating device, so that such heat flow continuously changes exclusively according to the distance between the wick and the heating device.

These and other objects are achieved, according to the present invention, by means of a vaporiser having the features described in the main claim. Other features of the invention are described in the dependent claims.

Further features and advantages of the present invention will in any case become more evident from the following detailed description of a preferred embodiment of the same, taken with reference to the accompanying drawings, wherein:

FIG. 1 is an elevation front view of the vaporiser according to the present invention in an intermediate adjustment position;

FIG. 2 is a cross-section view of the vaporiser of FIG. 1, along line II—II of the same drawing;

FIG. 3 is an enlarged-scale view of the detail encircled in FIG. 2;

Figure 5:
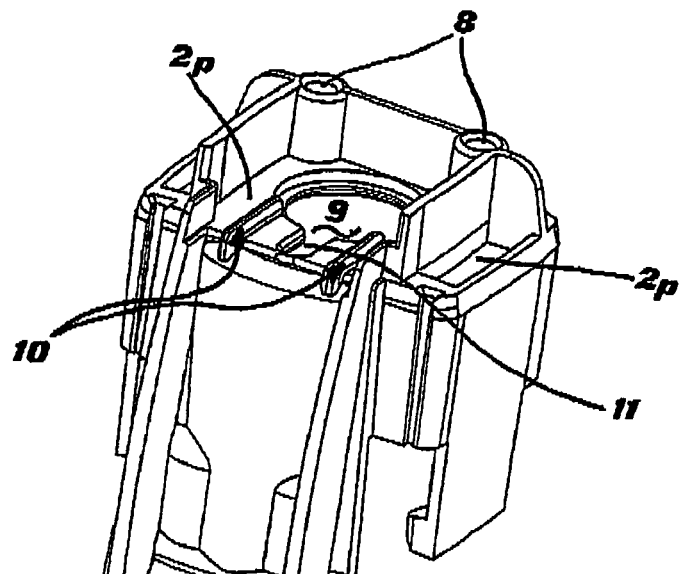
Figure 7:
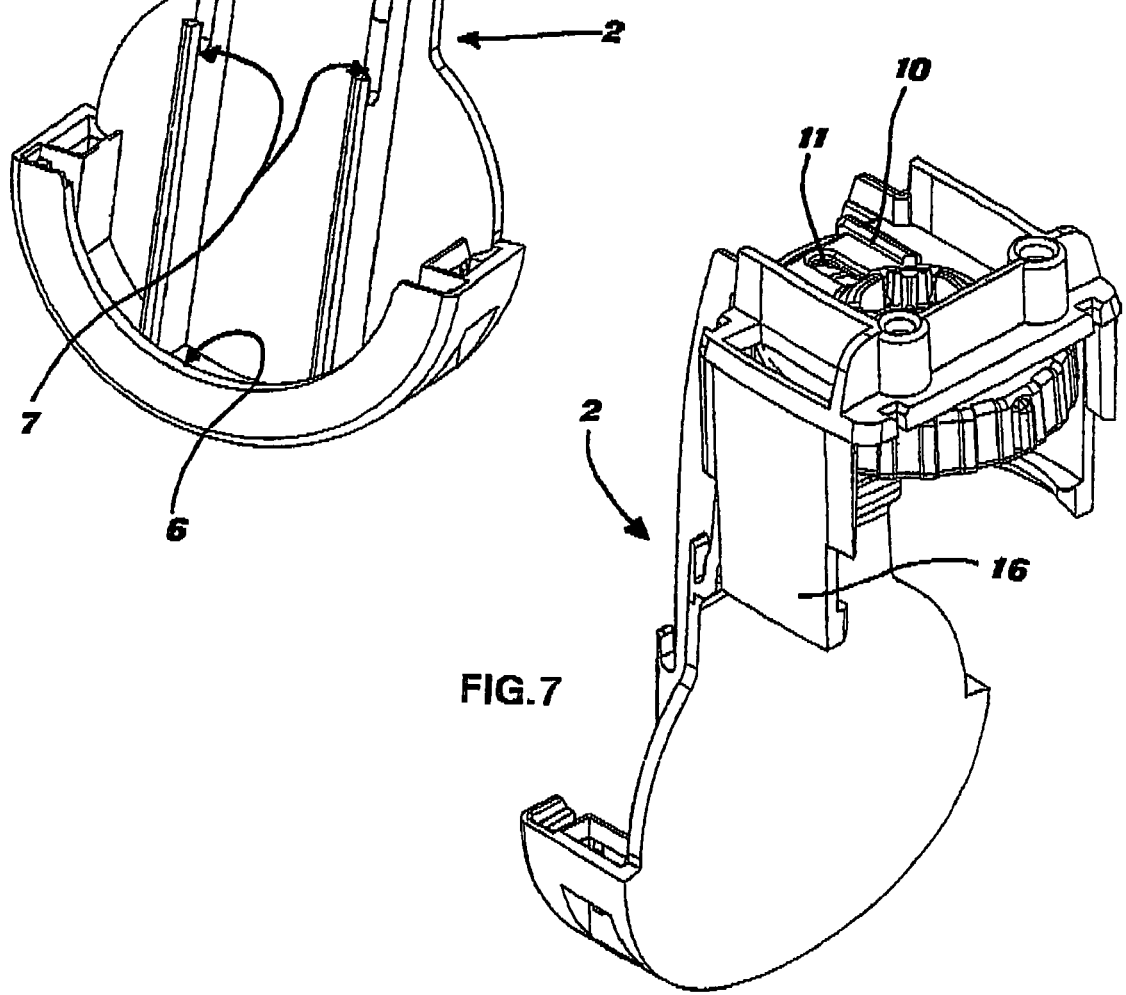

FIG. 3min is a similar view to FIG. 3, wherein the vaporiser is adjusted on minimum flow;

FIG. 3max is a similar view to FIG. 3, wherein the vaporiser is adjusted on maximum flow;

FIG. 4 is a bottom plan view of the vaporiser of FIG. 1, with no bottle containing the active substance;

FIG. 5 is a perspective view of the inner technical body of the vaporiser, plug side;

FIG. 6 is a perspective view in an enlarged scale of the vaporiser adjustment disc;

FIG. 7 is a perspective view of the inner technical body of the vaporiser, bottle side, with the adjustment disc mounted on the same; and FIG. 8 is a perspective view, in an enlarged scale, of the sliding drawer housing the electric heating device.

FIG. 1 shows an external view of the vaporiser of the present invention in a fully assembled condition, wherein it is possible to see the edge of an adjustment disc 1 slightly protruding from the contour of the vaporiser, from the bottle side view F. Adjustment of the evaporation intensity of the active substance occurs by rotating disc 1 between a position of minimum heat flow and one of maximum heat flow. Thanks to the special internal structure adopted—as will be clear in the following—the adjustment is such as to obtain a continuous variation of the evaporation intensity between the positions of minimum and maximum flow, thereby allowing correct and steady operation of the vaporiser with any desired intermediate evaporation intensity.

From the longitudinal section of the vaporiser, shown in FIG. 2, it is possible to gain a first overall view of the inner structure of the vaporiser and hence of the operation thereof. Such structure comprises a single inner technical body 2, onto which the different components of the vaporiser are assembled, more specifically: adjustment disc 1, a slidable drawer 3 housing an electric heating device R, a casing top C and a rotary plug S. Upon use, bottle F containing the active substance is finally inserted in the vaporiser, within which bottle a wick W is housed which crosses the whole height of bottle F and comes out of the neck of the same by a portion sufficient to position itself opposite the drawer 3 containing the heating device, i.e. precisely in the evaporation area of the vaporiser.

Said evaporation area is shown in greater detail in FIG. 3, wherein it is possible to see how, due to the adjustment, the slidable drawer 3 containing heating device R shifts parallel to itself in a direction perpendicular to the axis of wick W, between a position of longest distance from the wick W and hence of minimum evaporation intensity (FIG. 3min—wherein the outer wall of drawer 3 is at a distance of about 3 mm from the wick) and a position wherein the outer wall of drawer 3 is virtually touching the wick (FIG. 3max) and the vaporiser is hence capable of providing maximum evaporation intensity of the active substance. It will be noticed from the drawings that in addition to drawer 3 the evaporation area contains no mobile component, nor any other element, fixed or mobile, which can varyingly shield or alter the heat flow coming from heating device R, in all the different positions in which drawer 3 can be arranged. This means that the heat flow reaching wick W depends exclusively on the distance between said wick and chamber 3 and can therefore be precisely and continuously adjusted by varying the position of drawer 3. As a result, also the evaporation intensity of the active substance can be adjusted with the same continuity and effectiveness.

The regular and continuous shifting of drawer 3, upon varying of the position of disc 1, is obtained by slidingly engaging a guide pin 4, abutting on the lower side of drawer 3 and integral with the same, with a curved eyelet 5 having a variable radius, provided in disc 1, which eyelet hence acts as an adjustment cam of the position of said pin 4 upon varying of the angular position of the adjustment disc 1. Pin 4 is clearly visible in FIGS. 3 and 4, and is illustrated in a larger scale and in further detail in FIG. 8; the special shape of curved eyelet 5 is illustrated instead both in the same FIG. 4 and, in a larger scale and in greater detail, in FIG. 6.

Overall and perspective views of the inner technical body 2 only of the vaporiser are shown in FIGS. 5 and 7. In FIG. 5 the technical body 2 is shown from the plug side; therein the lower circular half-seat 6 for rotary plug S, a double plug-in seat 7 for top C, and a pair of threaded holes 8 for fixing said top to body 2 are clearly visible. In the upper part of technical body 2, at a substantially plane and horizontal wall 2p of the same, a hole 9 for housing adjustment disc 1 and, next thereto, a pair of ribs 10 which act as a guiding track of drawer 3 of heating device R are further formed. In a central position between the two ribs 10, and parallel to the same, a rectilinear eyelet 11 is finally formed, within which pin 4 of drawer 3 is housed. Technical body 2 is formed as a single piece by a suitable injection-molding process of plastic materials.

Adjustment disc 1 is shown in an enlarged scale in FIG. 6, where it can be appreciated, in addition to the already-described curved eyelet 5, that the disc side surface—in the area thereof protruding from the casing top C of the vaporiser through a suitable window obtained therein—has quite a pronounced knurling 13, for a good grip by the user, inside which a raised ratchet 14 is formed, which acts as an indicator of the position of disc 1 with respect to an external scale of reference drawn on top C. Disc 1 finally has a central hole, for housing wick W, around which multiple raised circle sectors are found. Part thereof, and specifically the three sectors 15f, are fixed and form the rotation reference for disc 1 on the edge of hole 9 of technical body 2, within which said sectors are fitted with slack; another part of the sectors instead, and specifically the three sectors 15e arranged alternately to sectors 15f, is capable of a modest elastic excursion in a radial direction, and has a free hook-shaped end, so that by pushing disc 1 against wall 2p of the body 2 wherein hole 9 is formed, the hook-shaped elastic elements 15e enter said hole by elastically bending and then return into their original position snapping up and enclosing the edge of hole 9 inside their hook area, thereby ensuring a steady positioning of adjustment disc 1. The technical body 2 with the adjustment disc mounted on the same is shown in FIG. 7, where body 2 is viewed from the side opposite to the one of FIG. 5, i.e. from the side where bottle F is inserted; in this view, two elastic arms 16, projecting downwards from body 2, for hooking up bottle F, are clearly visible. As is better visible in FIG. 1, the final mounting position of adjustment disc 1 onto technical body 2 is such that, when bottle F is mounted in the vaporiser, adjustment disc 1 is positioned at the mouth of said bottle.

Finally, FIG. 8 shows the slidable drawer 3 of heating device R, essentially consisting of a parallelepipedal block centrally provided with a recess 17 for housing a heating device R, such as a resistance or a PTC. The drawer 3 is further provided, in the bottom part thereof, with the already-described protruding pin 4. Pin 4 has a cylindro-conical annular rib 18 which separates a central portion 4r thereof, intended to slidingly engage with the rectilinear eyelet 5 of body 2 of the vaporiser, from an end portion 4c intended instead to slidingly engage with the curved eyelet 5 of adjustment disc 1. The special shape of annular rib 18 allows on the one hand to easily insert the same into rectilinear eyelet 11, due to the elastic deformation of the latter, thanks to the draft represented by the tapered part of the rib and, on the other hand, to form a steady retention with the cylindrical portion thereof in order to maintain drawer 3 steadily positioned in a vertical direction with respect to body 2, during shiftings of the same in a horizontal direction. There is further to be appreciated that the side walls of drawer 3 extend downwards, beyond the bottom plane of the drawer, forming two parallel abutting portions 19, apt to cooperate externally with the guiding track formed by ribs 10 provided on body 2.

The combined action of the coupling between ribs 10 and abutting portions 19 on the one hand, and of the coupling between pin 4 and rectilinear eyelet 11 on the other hand, causes the shiftings of the slidable drawer 3 to occur exclusively on a horizontal plane and with no drawer rotation. Thereby, not only a long mechanical life of the device is guaranteed, but also that the variation of the heat flow reaching the wick evaporation area depends exclusively on the distance between the wick W and the drawer 3 and hence not on flow variations resulting from orientation variations of resistance R or of the walls of drawer 3 wherein it is housed.

Operation of the vaporiser described above is fully intuitive. As a matter of fact, once bottle F has been inserted into body 2 of the vaporiser and blocked in its seat, and plug S has been inserted in an electric socket, it is sufficient to rotate disc 1 from outside the vaporiser in order to obtain the desired shifting of drawer 3, and hence of resistance R contained therein, into a position more or less close to the wick, consequently varying evaporation intensity. Since the coupling between curved eyelet 5 and pin 4 is not of the reversible type, once the vaporiser has been adjusted in a desired operation position, it remains perfectly steady in such position.

It will finally be noticed that the special arrangement of drawer 3 in respect of plug S causes a rather lengthy portion 20 of the electrical connection wires to be formed, having a direction substantially perpendicular to the shifting direction of drawer 3. By this arrangement it is hence obtained that the shifting of the ends of the connection wires connected with resistance R, resulting from the shiftings of drawer 3, is absorbed by the shape elasticity of wire portion 20, without affecting in the least the electrical connections to plug S. The vaporiser according to the present invention is hence characterised also by a high degree of electric operation safety over time.

Thanks to the various features described above, the vaporiser of the present invention has thereby achieved all the objects of the present invention. It has in fact an extremely simple and compact mechanical structure, both in terms of construction of the single components, and in terms of mounting the same, which mounting can hence be easily automated. Moreover, no element, fixed or mobile, is present in the evaporation area, between drawer 3 and wick W, while drawer 3 always moves perfectly parallel to itself, so that the variation of the heat flow spreading over the wick only depends on the distance between the wick W and the resistance R, and varies continuously therewith. Furthermore, thanks to the precision of the system moving drawer 3, the movement of the same repeats itself identically at each adjustment operation, so that the adjustment effect is optimally repeatable over time. Finally, the electrical connections of the resistance are arranged so as to guarantee their longer duration and safety despite the movement which is imparted to the same by the adjustment movement of drawer 3.

The vaporiser of the present invention has been described with reference to a preferred embodiment of the same, but it is obvious that a number of variants of such vaporiser can be devised, all within the reach of an expert in the field, without departing from the scope of protection of the invention, which is hence defined exclusively by the accompanying claims.

The invention claimed is:

1. Electric vaporiser of a fragranced or insecticidal active substance with adjustment of the evaporation intensity, comprising a support technical body (2), a porous element (W) impregnated with said active substance and an electric heating device (R) located in the proximity of said porous element (W) in order to determine the evaporation of the active substance in an evaporation area, said porous element (W) and said electric heating device (R) being fixed to said support body (2), characterised in that said electric heating device (R) is movable in a direction substantially perpendicular to said porous element (W) between a position of maximum evaporation intensity, near or adjacent to the porous element (W), and a position of minimum evaporation intensity, far from the porous element (W), and in that the control mechanism which causes the shifting of the electric device (R) is located outside said evaporation area.

2. Electric vaporiser as in claim 1, wherein said porous element is the protruding portion of a wick (W) sunk in a bottle (F) containing said active substance in a liquid formulation.

3. Electric vaporiser as in claim 2, wherein said electric device (R) is housed in a drawer (3) which is movable between said positions.

4. Electric vaporiser as in claim 3, wherein said drawer is slidable along rectilinear ribs (10) formed in the support body (2) of the vaporiser with which parallel abutting portions (19) engage, the movement of the drawer (3) being driven by the coupling between a pin (4) protruding from said drawer (3) and a variable-radius guiding cam (5) formed in an adjustment disc (1).

5. Electric vaporiser as in claim 4, wherein said pin (4) cooperates with said variable-radius guiding cam (5) at an end portion (4c) thereof, while being guided by a mid-portion (4r) thereof into a rectilinear eyelet (11) formed in the vaporiser body (2), which is parallel to said rectilinear ribs (10).

6. Electric vaporiser as in claim 5, wherein said mid-portion (4r) and end-portion (4c) of the pin (4) are separated by an annular cylindro-conical rib (18) which serves firstly as a draft and secondly as a retention in respect of said rectilinear eyelet (11).

7. Electric vaporiser as in claim 4, wherein said adjustment disc (1) is coaxial to said wick (W) and has a hole for the same to pass through.

8. Electric vaporiser as in claim 7, wherein said adjustment disc (1) is fixed to said vaporiser body (2) at the mouth of the bottle (F).

9. Electric vaporiser as in claim 8, wherein,
said adjustment disc hole is a through-hole for the wick (W), and
said adjustment disc (1) has, around the through-hole for the wick (W), a series of raised circle sectors (15) for the freely rotatable coupling with a corresponding hole (9) formed in the vaporiser body (2), on the same plane and horizontal wall (2p) wherein the rectilinear ribs (10) and eyelet (11) for guiding the drawer (3) are formed.

10. Electric vaporiser as in claim 4, wherein the drawer (3) containing the electrical device (R), and the adjustment disc (1), are mounted on opposite sides in respect of said plane and horizontal wall (2p) of the vaporiser body (2), so that the adjustment disc (1) lies on the same side of the bottle (F) with respect to said plane and horizontal wall (2p).

11. Electric vaporiser as in claim 9, wherein said raised sectors (15) partly form (15f) a fixed rotation abutment and partly (15e) a system for an elastic hook retention of the adjustment disc (1) in said hole (9) formed in the plane and horizontal wall (2p) of the vaporiser body (2).

12. Electric vaporiser as in claim 1, wherein a lateral surface of said adjustment disc (1) has a pronounced knurling (13) at the front of the vaporiser, said knurling (13) partly protruding from an outer casing top (C) of the vaporiser through an aperture obtained therein.

13. Vaporiser as in claim 1, wherein said electric heating device (R) is an electric resistance or a PTC.

14. Vaporiser as in claim 1, wherein electric wires connecting the electric heating device (R) to the plug (S) have a fairly long portion (20) running in a direction substantially perpendicular to the direction of movement of the drawer (3) containing said electric heating device.

* * * * *